(12) United States Patent
Ward et al.

(10) Patent No.: US 8,126,233 B2
(45) Date of Patent: Feb. 28, 2012

(54) IMAGE RECONSTRUCTION FOR UNORDERED MICROWELL PLATES

(75) Inventors: Kenneth Ward, Corvallis, OR (US); Kevin F. Peters, Corvallis, OR (US)

(73) Assignee: Hewlett-Packard Development Company, L.P., Houston, TX (US)

(*) Notice: Subject to any disclaimer, the term of this patent is extended or adjusted under 35 U.S.C. 154(b) by 498 days.

(21) Appl. No.: 12/476,168

(22) Filed: Jun. 1, 2009

(65) Prior Publication Data

US 2010/0303312 A1 Dec. 2, 2010

(51) Int. Cl.
*G06K 9/00* (2006.01)
(52) U.S. Cl. ........................ 382/128; 382/133
(58) Field of Classification Search .................. 382/128, 382/133
See application file for complete search history.

(56) References Cited

U.S. PATENT DOCUMENTS

| | | | |
|---|---|---|---|
| 6,913,935 B1* | 7/2005 | Thomas | 436/518 |
| 7,978,885 B2* | 7/2011 | Arini et al. | 382/128 |
| 2001/0024796 A1* | 9/2001 | Selifonov et al. | 435/7.1 |
| 2005/0002552 A1* | 1/2005 | Dunn et al. | 382/133 |
| 2005/0207633 A1* | 9/2005 | Arini et al. | 382/133 |

* cited by examiner

*Primary Examiner* — Joseph Chang (57) ABSTRACT

The present invention is embodied in an image reconstruction method for analyzing unordered microwell plates, including acquiring a digital image of a microwell plate showing unordered visible compound concentration effects, creating a dispensing log listing the dispensing log information for an unordered microwell plate, establishing one or more rules to govern the reorganization of the unordered visible digital image, creating a reordered log with well input locations reordered by test compound identity and quantity levels dispensed order corresponding reordered log well output locations, assigning ordered output locations to reordered input compound and concentration levels order and copying test well digital image pixels from well input locations to reordered output locations in a reconstructed digital image for visualization of visible compound effects in the microwell plates in ordered compound concentrations.

20 Claims, 6 Drawing Sheets

IMAGE RECONSTRUCTION FOR UNORDERED MICROWELL PLATES

BACKGROUND

Normally compounds are dispensed into microwell plates in an orderly layout in order of concentration or in some other ordered sequence. This is for ease of use of conventional dispensing equipment. This is also for visualization of compound effects, either directly in the microwell plates or using data obtained from the microwell plates represented visually such as by using false color. Dispensing of compounds into microwell plates can be more preferably performed by randomizing the dispense order throughout the microwell plate in order to decouple systematic effects such as the dispense order or edge effects from the effects of compounds themselves. However, many researchers still prefer to visualize chemical or biological effects with ordered positions. Randomized microwell plate dispense designs have not been used because of the limitations of conventional analog dispense methodologies and the desire for visualization.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized and structural changes may be made without departing from the scope of the present invention.

Figure 1:
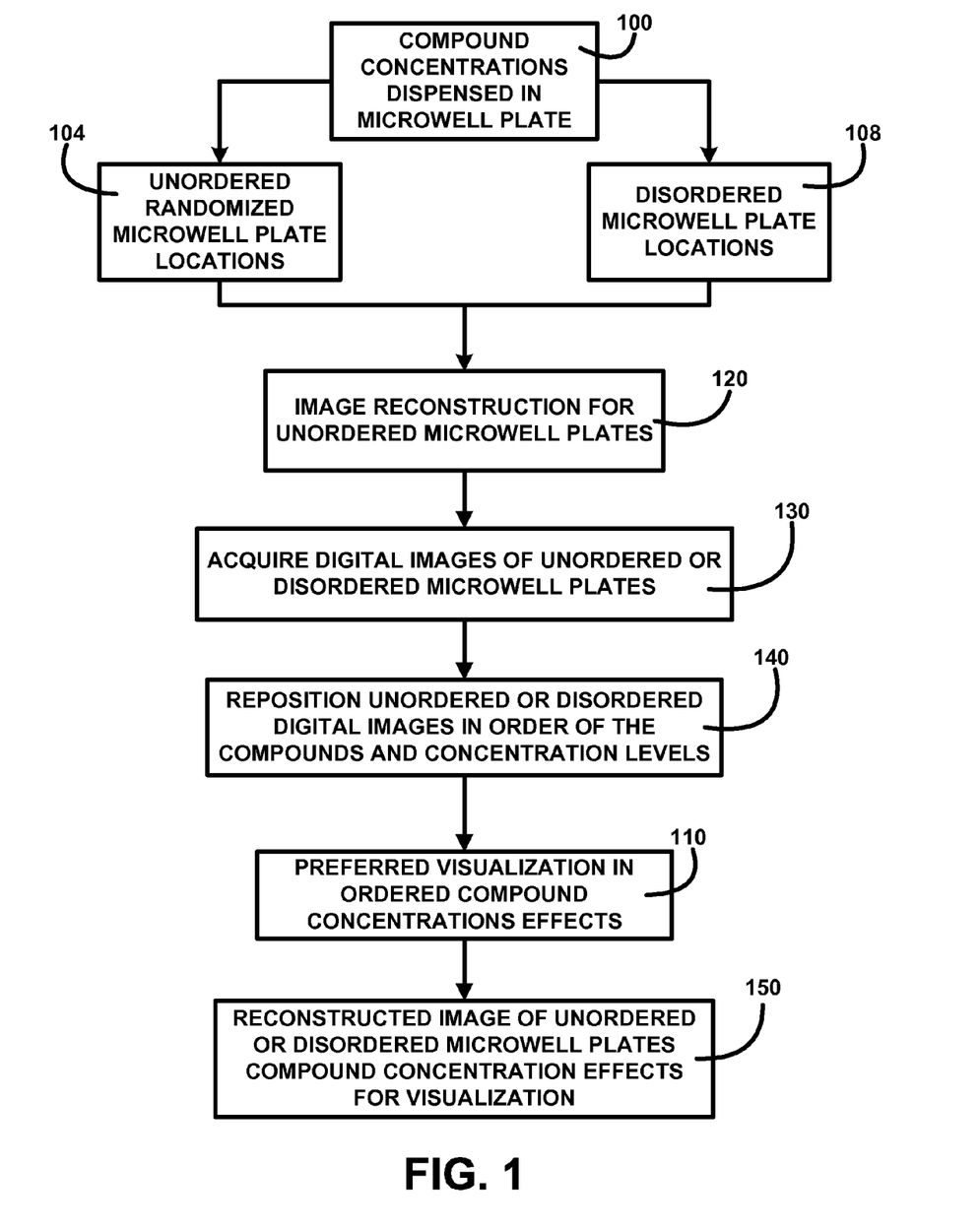
FIG. 1 shows a block diagram of an overview of an image reconstruction for unordered microwell plates method in one embodiment of the present invention.

General Overview:

In general, FIG. 1 shows a block diagram of an overview of an image reconstruction system for unordered microwell plates in one embodiment of the present invention. In one embodiment, the image reconstruction are used for dispensed solutions, such as drug compounds, chemicals, bio-chemicals, and biologics (hereinafter referred to as "compounds" for simplicity), into microwell plates. Solutions are dispensed into the microwell plate wells according to a systematic layout, such as from high concentration to low concentration along the rows of the microwell plate. In one embodiment, the compounds are dispensed according to a time sequence, such as from first to last at prescribed time intervals. In one embodiment, the chemical or biological effects are visualized in the microwell plates by using visible or falsely colored indications with dispensed positions in sequential order of the compounds and concentration levels.

Namely, FIG. 1 shows compound concentrations dispensed in microwell plate 100 in both unordered randomized microwell plate locations 104 and disordered microwell plate locations 108. Compound concentrations can be dispensed in a disordered manner or in a specialized form of disordering by randomization. The visualization of ordered compound concentrations effects 110 desired by researchers is used for analysis of for example chemical or biological effects in microwell plates. The visualization of ordered compound concentration effects 110 can be generated in any desired visualization pattern by the user, or can be automatically generated from the known compound identities and concentrations using automated software methods. In embodiments where other disordered variations may be implemented, then the visualization can be generated from the known disordered variation.

In one embodiment, the compounds are dispensed into microwell plates 100 by randomizing the dispense layout and order throughout the microwell plate test wells 104 in order to decouple the chemical effects from the dispense order and from other systematic errors such as edge effects, environmental changes, chemical gradients, component reactions, cross contamination, contaminant increases, compound adsorption, diffusive or other kinetic variations, and other time- or layout-based effects in the dispenser, its source or its destination. In one embodiment, image reconstruction for unordered microwell plates 120 uses digital images of the microwell plate 100 having unordered compound effects resulting from randomized dispensing and rearranges the digital images in the orderly layout or other sequential order of the compounds and concentration levels desired by the researchers for visualization.

In one embodiment, a disordered image of microwell plate wells 104 is reorganized according to compounds and their sequence of concentrations. It is to be understood that other systematic variations, as aforementioned, may be implemented in a disordered fashion, imaged, and subsequently reorganized according to the present invention.

In one embodiment, the unordered microwell plates 120 of FIG. 1 are visualized from the unordered, dispensed microwell plates by digital imaging. Specifically, a digital image of a microwell plate with unordered compound concentration effects 130 is captured. The input location information from the disordered or random dispensing is reordered according to compound concentration, and the reordering is applied to the image to reposition input locations from unordered digital images into the output image in order of the compounds and concentration levels 140.

The reordering and repositioning can be generated from a stored map of the visualization, such as may be generated upon initially disordering or randomizing the positions. Alternatively, the reordering and repositioning can be generated from a rule for the visualization, such as from high concentrations to low concentrations; by increasing alphanumerical identifier of the compounds, by decreasing potency of the compounds as revealed by analysis of the image data, or by combinations of rules. The portion of the digital image for each test well is copied from its original input location to a new ordered output position in a reconstructed image of unordered microwell plate compound effects for visualization 150 in one embodiment of the present invention. Hence, the method for visualization of compound effects from an unordered dispense order is achieved by allowing both the optimized scientific practices for dispensing and for treatment of systematic variations, while end-user availability of the desired analytical visualization is preserved.

Figure 2:
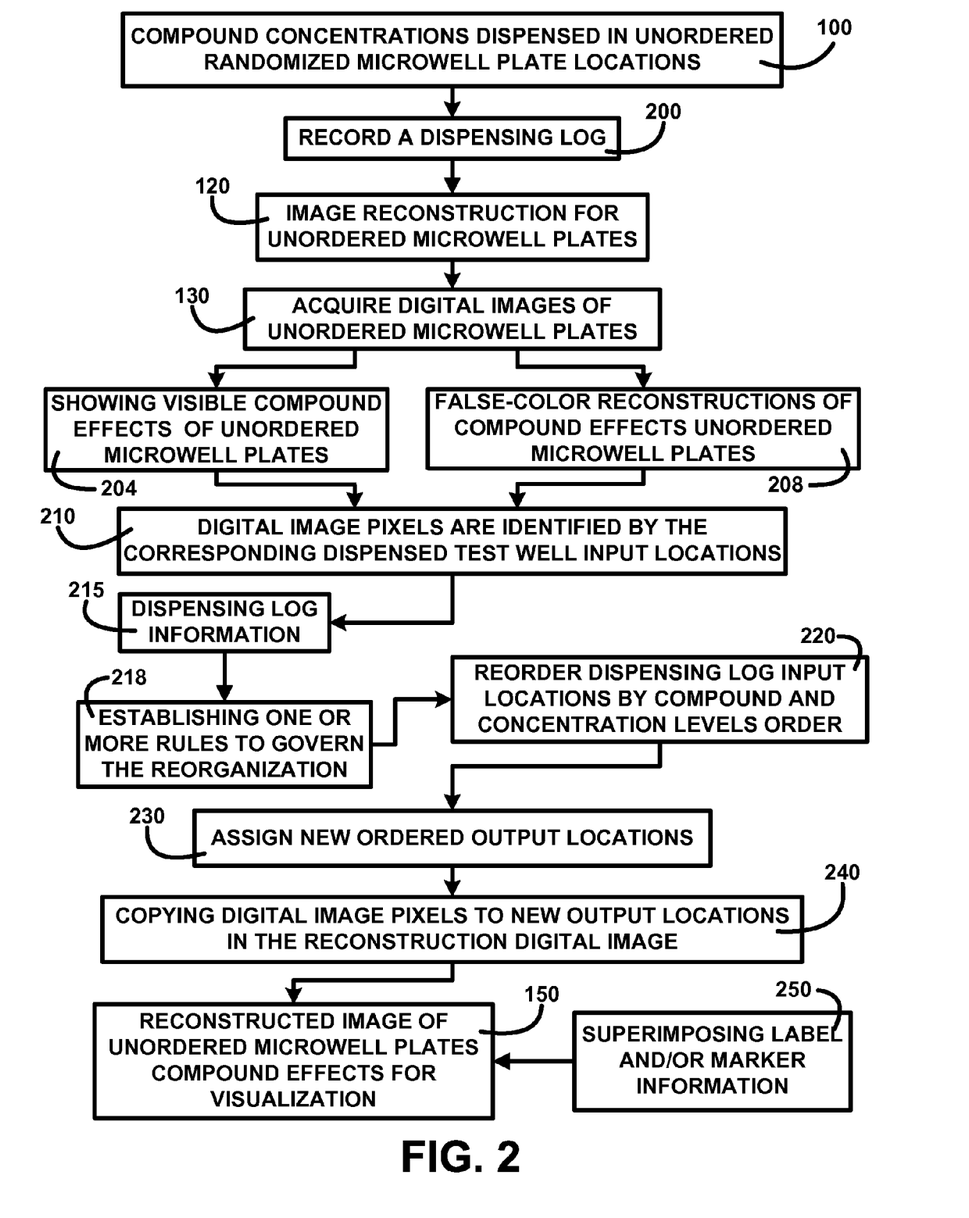
FIG. 2 shows a flow chart of an image reconstruction for unordered randomized microwell plates method in one embodiment of the present invention.

Detailed Operation:

FIG. 2 shows a flow chart for reconstructing unordered microwell plates in one embodiment of the present invention. Initially, compound concentrations dispensed in unordered randomized microwell plate locations 100 are provided. Randomized microwell plate dispensing can be performed by conventional analog dispensing methodologies. Also, manual dispensing or numerous changes of compound solution concentrations can be used to perform the randomization. Moreover, digital dispensing can be used to enable these randomized dispense patterns to be performed easily and automatically in one embodiment.

After randomized wellplate dispensing, a dispensing log 200 is recorded. The dispensing log includes, for example, a microwell plate identifier, the test well location on the microwell plate, the compound being dispensed and the quantity of the compound dispensed into each test well, which determines the concentration level. This is when the image reconstruction for unordered microwell plates 120 of FIG. 1 process begins in one embodiment.

Each type of testing may require different time intervals for the reaction or reactive results to be completed. After the dispensing operation is complete and once the testing results are ready, a digital image of a microwell plate with unordered compound concentration effects 130 of FIG. 1 is captured. The digital image pixels for each well are identified using manual plate alignment processes and the known well boundaries of standard well plates in one embodiment. The microwell plate digital image pixels can also be identified automatically, by using standard image processing techniques.

In one embodiment, digital images of false-color reconstructions of unordered microwell plates 208 are acquired. When the digital images of the false-color reconstructions of unordered microwell plates 208 are generated, information regarding the false-color application can additionally be recorded. For example, the colors can represent the compounds that are used and different colors applied to different quantities dispensed. The dispensing log information 215 which is used for the digital reconstruction is guided by establishing one or more rules to govern the reorganization 218 of the digital images.

The recorded dispensing log information 215 is used to reorder dispensing log input locations by compound and concentration levels order 220 in one embodiment. The process proceeds to assign new ordered output locations 230 to the corresponding reordered compound and concentration levels input locations. The correspondence between the original input position and the output position is used for copying digital image pixels to new output locations in the reconstructed digital image 240. A boundary of the digital image pixels for each test well location of an acquired digital image can be used when determining which digital image pixels should be copied.

In one embodiment, the reconstructed digital image contains additional information by superimposing label and/or marker information 250 for example chemical identities or compound quantities dispensed. The reconstructed image from unordered microwell plates enables visualization of compound effects using the reconstructed image 150 of FIG. 1. The reconstructed image 150 of FIG. 1 allows the effects of compounds based on concentration levels to be readily visualized and the deleterious systematic effects to be minimized through randomized compound dispensing distributions in microwell plates in one embodiment.

It should be noted that the specific use above of compound and concentration levels is a non-limited example of the rules by which reordering may be accomplished. The time of dispense or the compound potency data are other examples. It is also noted that the reordering according to rules is a general example. In one embodiment, a rule that is the reverse mapping of a prior disordering is used. This embodiment has the advantage of restoring the visualization that the end-user may have conceived in initially preparing the experiment, prior to disordering.

Figure 3:
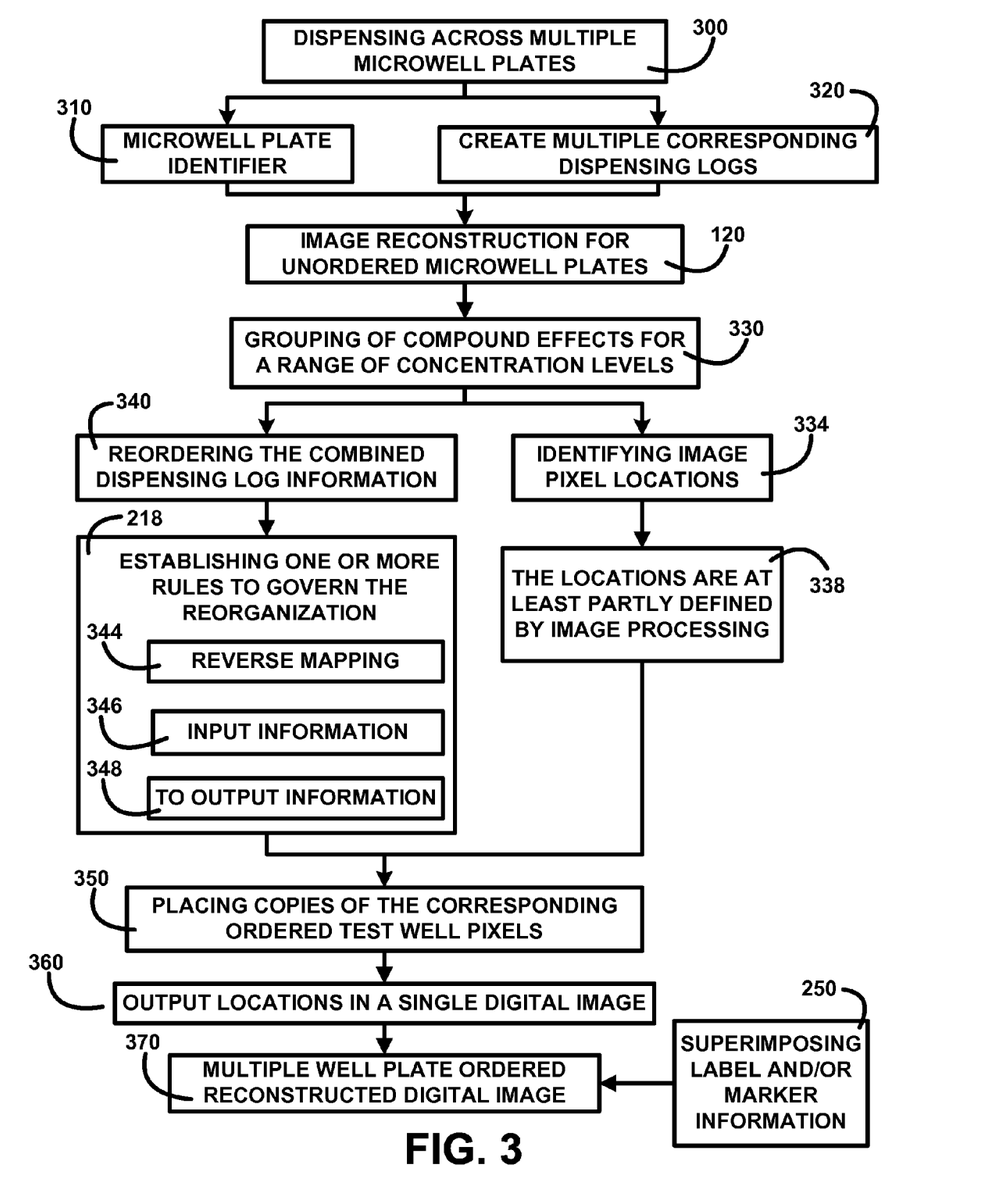
FIG. 3 shows a flow chart of an image reconstruction for multiple unordered disordered or randomized microwell plates method in one embodiment of the present invention.

Image Reconstruction for Multiple Unordered Microwell Plates:

FIG. 3 shows a flow chart of an image reconstruction for multiple unordered disordered or randomized microwell plates in one embodiment of the present invention. FIG. 3 shows image reconstruction for unordered microwell plates 120 of FIG. 1 where disordered or randomized dispensing across more then one or multiple microwell plates 300. In one embodiment, large numbers of concentrations or compounds being tested are used. A microwell plate identifier 310 is used to identify multiple microwell plates when dispensing of a test solution is done across more than one microwell plate. The dispensing information used in a multi well plate dispensing process for each microwell plate is used to create multiple corresponding dispensing logs 320.

Digital images of the multiple unordered microwell plates are captured and are used along with the corresponding dispensing logs information for the image reconstruction for unordered microwell plates 120 of FIG. 1. An ordered reconstructed digital image for a range of concentration levels can be assembled by reordering the combined dispensing log information 340 and identifying test well image pixels by location within unordered digital images. A grouping of compound effects for a range of concentration levels 330 is identified that will fit in a single reconstructed digital image. Reordering includes identifying image pixel locations 334 by the microwell plate identifier 310 and the locations are at least partly defined by image processing 338.

The combined dispensing log information 340, which is used for the digital reconstruction, is guided by establishing one or more rules to govern the reorganization 218 of the digital images. In one embodiment, a rule is the reverse mapping 344 of the disordering from a prior layout; also a rule according to input information 346 for example concentration, compound identifier, or time of dispense and a rule according to output information 348, such as time of image creation, compound potency, or a property of the images at the locations. The established rules are used in assigning ordered output locations.

An ordered reconstructed digital image for a range of concentration levels is assembled 340 by placing copies of the corresponding ordered test well pixels 350 in output locations in a single digital image 360 for a selected grouping of compound effects. The reconstructed digital image can contain additional information by superimposing label and/or marker information 250 for example chemical identities or compound quantities dispensed. A multiple well plate ordered reconstructed digital image 370 is then ready for visualization in one embodiment of the present invention.

Example of Unordered Compound Effects in a Microwell Plate:

In one embodiment, compounds are dispensed into microwell plates for testing purposes for scientific research. For illustrative purposes only, FIG. 4A and FIG. 4B shows an example of microwell plates with multiple test compounds for determining compound effects on biological organisms of one embodiment in one embodiment of the present invention and an example of a digital image of unordered compound effects after dispensing compound concentrations in randomized test well locations in a microwell plate in one embodiment of the present invention.

Figure 4A:
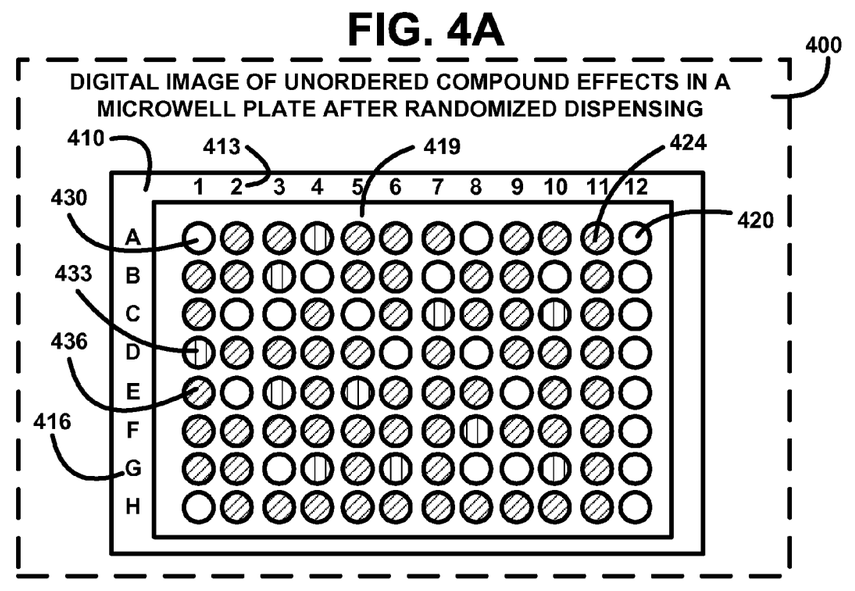
FIG. 4A shows for illustrative purposes only shows an example of a digital image of unordered compound effects after dispensing compound concentrations in randomized test well locations in a microwell plate in one embodiment of the present invention.
Figure 4B:
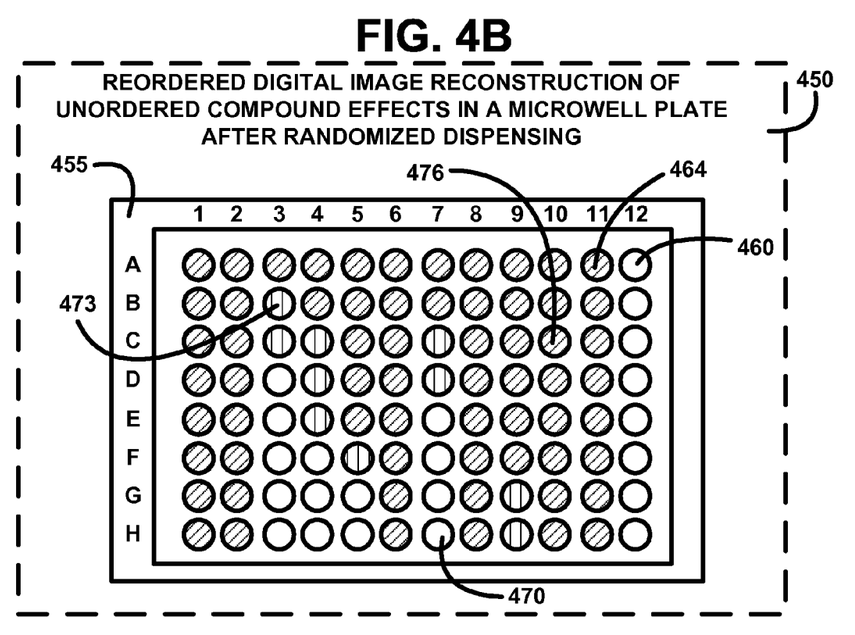
FIG. 4B shows for illustrative purposes only shows an example of a reordered reconstruction of a digital image of unordered compound effects from a microwell plate after a randomized dispensing operation in one embodiment of the present invention.

FIG. 4A shows an illustrative example of a digital image of unordered compound effects in a microwell plate after randomized dispensing 400 in which the compound effects are in the unordered input position. This shows a microwell plate 410 after the unordered dispensing. Standardized microwell plates generally have microwell plate column identification numbers 413 and microwell plate row identification letters 416 that are used to identify the location of each microwell plate test well 419 in one embodiment.

Test control wells are located in columns 11 and 12. A control group of test wells in column 11 shows biological organisms alive 420 and a control group of test wells in column 12 shows biological organisms dead 424. These act as compound effect test controls for comparison to varied concentrations of the compound in the remaining test wells. The test control solutions shown in columns 11 and 12 in FIG. 4A can also be dispensed in a randomized layout of the well plate and interspersed amongst the compound effects test well positions.

A test well in the row A and column 1 input location 430 of the microwell plate shows test compound effects of biological organisms alive for that particular test compound concentration level. A test well in the row D and column 1 input location 433 of the microwell plate shows test compound effects of biological organisms partially alive for that particular test compound concentration level. A test well in the row E and in column 1 input location 436 of the microwell plate shows test compound effects of biological organisms dead for that particular test compound concentration level. The unordered compound effects of FIG. 4A can be ordered, as discussed in detail with reference to FIG. 4B below.

Example of a Reconstructed Ordered Image:

FIG. 4B shows for illustrative purposes only an example of a reordered reconstruction of a digital image of unordered compound effects from a microwell plate after a randomized dispensing operation in one embodiment. FIG. 4B also shows microwell plate randomized dispensing results 450 in which the image of each test well is in a new ordered output position. The ordered output positions are determined from the chemical identities and compound concentrations of the dispense log. Shown in FIG. 4B is digital image of the microwell plate illustrated in FIG. 4A after the dispensing results are ready for visualization review 455. The digital images of the control group of test wells with biological organisms alive 460 are still shown in column 11 and digital images of the control group of test wells with biological organisms dead 464 are still shown in column 12 in one embodiment, where the columns do not have reordering.

The assigned reordered output locations corresponding to the original input positions are used for copying digital image pixels to new output locations in the reconstruction digital image 240 of FIG. 2. Test compound concentrations are reordered so that the concentrations are decreasing as the positions in columns 1 through 10 go from top to bottom or rows A to H.

The digital image copying places the digital image pixels for the test well in the row A and column 1 input location 430 of FIG. 4A into the output location at row H column 7 470. The test well in row D and column 1 input location 433 of FIG. 4A are placed into the output location at row B column 3 473, and the test well in the row E and in column 1 input location 436 of FIG. 4A is placed into the output location at row C column 10 476 in the reordered reconstruction image. Based on the reordered image in FIG. 4B, it can be visually determined that the compounds in columns 1, 2, 6, 8, and 10 maintain the biological organisms alive at all tested compound concentrations, whereas the compound in column 3, the biological organisms are maintained alive at only the highest compound concentration. Thus, as shown in FIG. 4B, the reordering provided significant visualization of the compound effects for the multiple test compounds at the different concentration levels.

This is accomplished once the digital images of the test wells have been reordered and the microwell plate image reconstruction is completed in one embodiment of the present invention. In one embodiment, reconstructed images can be reconstructed into formats that resemble the format of the original test microwell plate. It is also possible (not shown) to form a reconstructed image that has row, column, or well separation, for example, that may differ from the format of the original.

Figure 5:
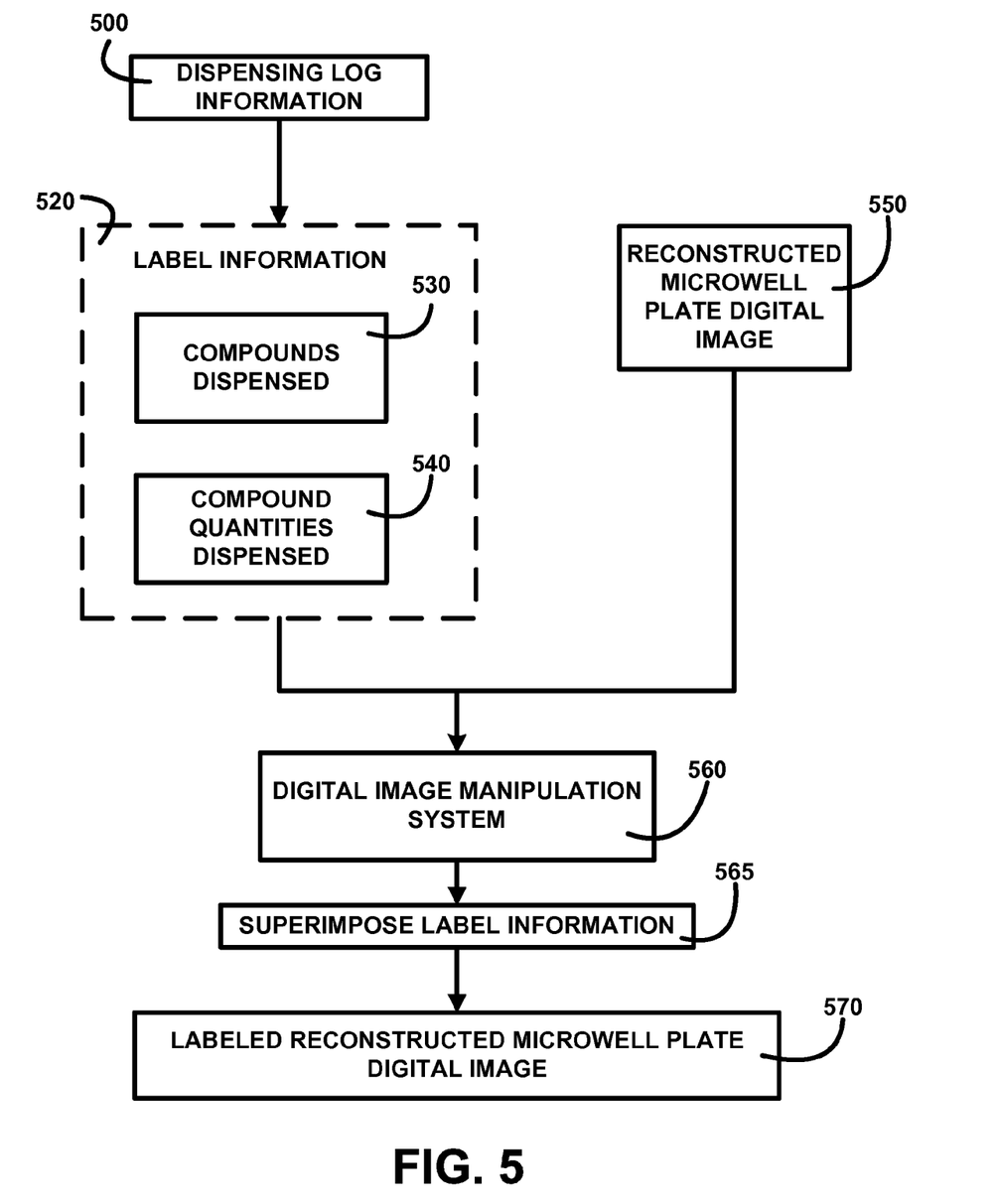
FIG. 5 shows a block diagram of a reconstructed image for unordered microwell plates labeling method in one embodiment of the present invention.

Labeling Reconstructed Images:

FIG. 5 shows a block diagram of a reconstructed image for unordered microwell plates labeling method of one embodiment of the present invention. FIG. 5 shows that a reconstructed digital image can easily be labeled with chemical identities or compound quantities dispensed. The dispensing log information 500 provides some of the label information 520 that can be included on the image. The label information 520 can be, for example, compounds dispensed 530 and the amount of compound quantities dispensed 540 in the microwell plate. A reconstructed microwell plate digital image 550 can be inputted into a digital image manipulation system 560. The label information 520 is entered and the system caused to superimpose label information 565 in the digital image. Last, the new labeled reconstructed microwell plate digital image 570 is then available for visualization with the desired information available in one embodiment of the present invention.

Figure 6:
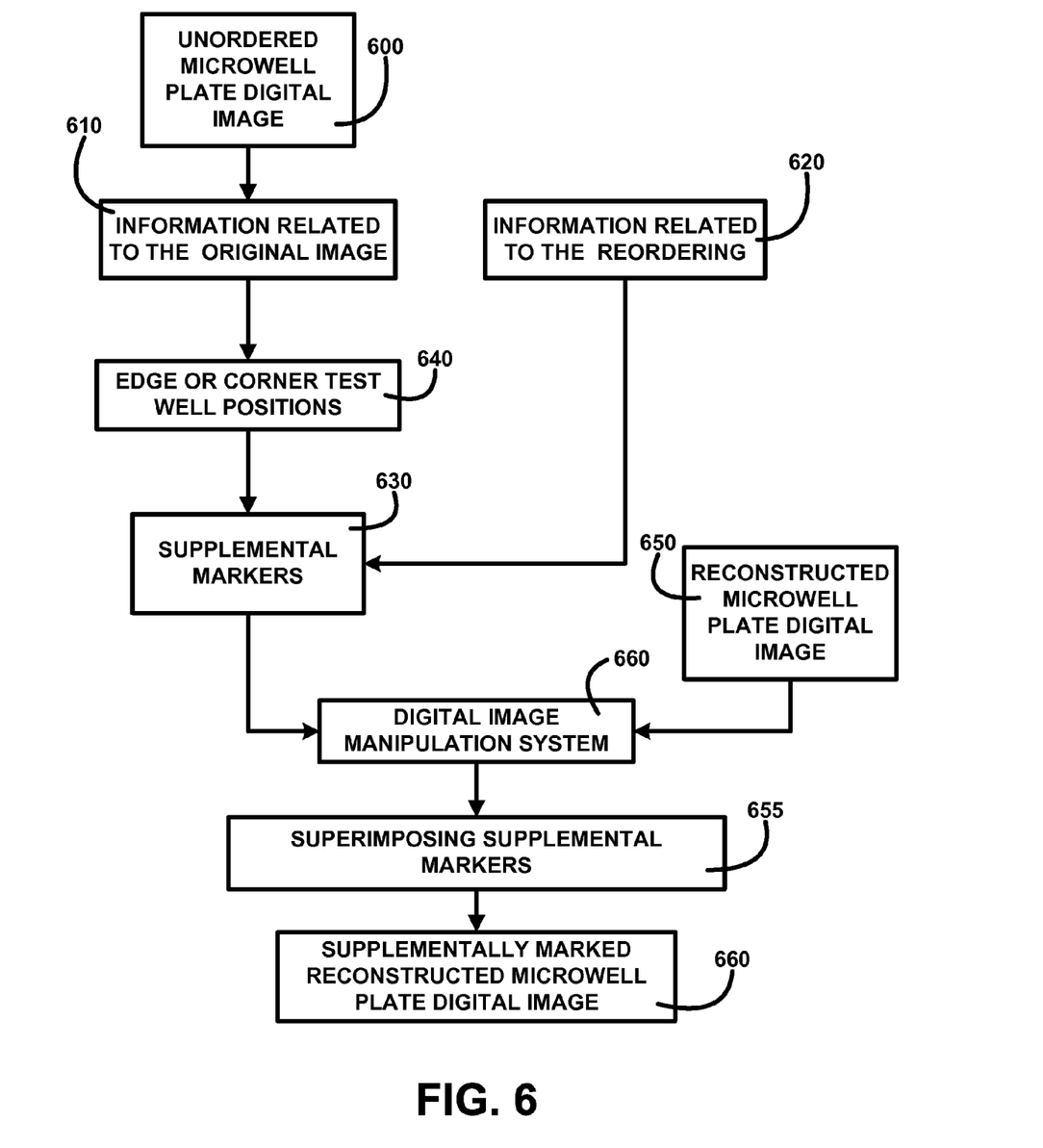
FIG. 6 shows a block diagram of a supplemental marking of a reconstructed image method in one embodiment of the present invention.

Supplemental Marking of Reconstructed Images:

FIG. 6 shows a block diagram of a supplemental marking of a reconstructed image method of one embodiment of the present invention. FIG. 6 shows information being gathered and developed from the unordered microwell plate digital image 600. Additional information related to the reordering 620 process can additionally be gathered. Examples of information related to the original image 610 can include time stamps or position characteristics of the test well locations such as corner positions and edge positions of the well plate. For example edge or corner test well positions 640 of a microwell plate may be used as the supplemental marker 630. These position marks and other information desired are supplemental markers 630 to be included on the ordered image.

The reconstructed microwell plate digital image 550 of FIG. 5 is inputted into a digital image processing system 560 of FIG. 5 and the supplemental markers 630 inputted for placement. The process continues to superimpose supplemental markers 655 in the reconstructed microwell plate digital image 550 of FIG. 5. A supplemental marked reconstructed digital image which will provide the researcher with information that can be useful in the visual analysis of the compound effects. The form of the supplemental markers 630 can be for example graphical symbols such as right angles to signify each of the four corners or other meaningful markings desired by a researcher to aid in the visual analysis in one embodiment.

The foregoing has described the principles, embodiments and modes of operation of the present invention. However, the invention should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. An image reconstruction method for analyzing unordered microwell plates, comprising:
   acquiring a digital image of a microwell plate showing unordered visible compound concentration effects;
   creating a dispensing log listing the dispensing log information for an unordered microwell plate;
   establishing one or more rules to govern the reorganization of the unordered visible digital image;
   creating a reordered log with well input locations reordered by test compound identity and quantity levels dispensed order corresponding reordered log well output locations;
   assigning ordered output locations to reordered input compound and concentration levels order; and
   copying test well digital image pixels from well input locations to reordered output locations in a reconstructed digital image for visualization of visible compound effects in the microwell plates in ordered compound concentrations.

2. The method of claim 1, further comprising superimposing digital labels associated with the dispensing log information and superimposing digital supplemental markers on a reconstructed digital image showing reordering process information and original image position locations.

3. The method of claim 1, wherein the locations of the unordered dispensed test well images are at least partly defined by using a digital image processing system to identify a boundary of the digital image pixels for each test well location within an acquired digital image.

4. The method of claim 2, wherein the superimposed digital labels associated with the dispensing log information show compound identity and quantity levels dispensed.

5. The method of claim 2, wherein superimposing digital supplemental markers show original image position characteristics of the test well locations such as corner positions and edge positions of the well plate.

6. The method of claim 1, further comprising using a microwell plate identifier to identify microwell plates, identifying digital image pixels for each unordered dispensed test well input location, wherein the output locations of the reordered output images in a reordered log are at least partly defined by using a digital image processing system, the plate identifier and an output location.

7. An image reconstruction method for unordered microwell plates from disordered or randomized dispenses across multiple microwell plates, comprising:
   creating multiple corresponding dispensing logs identified by a microwell plate identifier;
   capturing digital images of the multiple unordered microwell plates;
   using multiple digital images of unordered microwell plates along with the corresponding dispensing logs information for the image reconstruction;
   selecting a grouping of compound effects for a range of concentration levels that will fit in a single reconstructed digital image;
   establishing one or more rules to govern the reorganization of the digital images;
   reordering the combined dispensing log information identified by a microwell plate identifier;
   creating a reordered log with well input locations reordered by test compound identity and quantity levels dispensed order;
   identifying digital image pixels for each unordered dispensed test well input location;
   creating an ordered reconstructed output digital image for a grouping of compound effects for a range of concentration levels; and
   placing copies of the corresponding ordered test well pixels for a selected grouping of compound effects in output locations in a single reconstructed digital image for visualization of effects in the microwell plates in ordered compound concentrations.

8. The method of claim 7, further comprising superimposing digital labels associated with the dispensing log information and superimposing digital supplemental markers on a reconstructed digital image showing reordering process information and original image position locations.

9. The method of claim 7, wherein identifying the output locations of the reordered output images in a reordered log are at least partly defined by using a digital image processing system, the multiple plate identifier and corresponding dispensing log information.

10. The method of claim 7, wherein the rule is established for the reverse mapping of the disordering from a prior layout.

11. The method of claim 7, wherein a rule is established according to one of the following input information: concentration, compound identifier, or time of dispense.

12. The method of claim 7, wherein a rule is established according to one of the following output information: time of image creation, compound potency, or a property of the images at the locations.

13. The method of claim 8, wherein the superimposed digital labels associated with the dispensing log information show compound identity and quantity levels dispensed.

14. The method of claim 8, wherein superimposing digital supplemental markers show original image position characteristics of the test well locations such as corner positions and edge positions of the well plate.

15. An image reconstruction apparatus for unordered microwell plates, comprising:
   one or more digital images configured to show reconstructions of compound effects of unordered microwell plates compound effects;
   a dispensing log configured to list dispensing log information such as the plate identifier, the identity of the compounds being dispensed and the quantity of compound dispensed into each individual test well by location;
   a dispensing log configured to list information used to create a an unordered microwell plate;
   digital image pixels identified by the locations within the unordered dispensed test well images;
   one or more rules to govern the reorganization of the unordered digital image;
   a reordered log with well input locations reordered by test compound identity and quantity levels dispensed order corresponding reordered log well output locations; and
   a digital manipulator configured to copy test well digital image pixels from well input locations to reordered output locations to define a reconstructed digital image for visualization of visible compound effects in the microwell plates in ordered compound concentrations.

16. The image reconstruction apparatus of claim 15, further comprising superimposed digital labels associated with the dispensing log information and superimposed digital supplemental markers showing reordering process information and original image position locations, wherein the superimposed digital labels associated with the dispensing log information show compound identity and quantity levels dispensed.

17. The image reconstruction apparatus of claim 15, wherein identifying the output locations includes identifying reordered false-color output images in a reordered log that is at least partly defined by using a digital image processing system, the plate identifier and false-color dispensing logs information.

18. The image reconstruction apparatus of claim 16, wherein superimposing digital supplemental markers show original image position characteristics of the test well locations such as corner positions and edge positions of the well plate.

19. The image reconstruction apparatus of claim 15, wherein a dispensing log is configured to list false-colorization information that includes information of colors representing compounds, colors applied to different quantities being dispensed and colors applied to compound effects indications.

20. The method of claim 15, wherein a rule is established according to one of the following input information: plate identifier concentration, compound identifier, concentration false-color, compound false-color or time of dispense.

* * * * *

UNITED STATES PATENT AND TRADEMARK OFFICE
CERTIFICATE OF CORRECTION

| | | |
|---|---|---|
| PATENT NO. | : 8,126,233 B2 | Page 1 of 1 |
| APPLICATION NO. | : 12/476168 | |
| DATED | : February 28, 2012 | |
| INVENTOR(S) | : Kenneth Ward et al. | |

It is certified that error appears in the above-identified patent and that said Letters Patent is hereby corrected as shown below:

In column 8, line 57, in Claim 15, delete "a an" and insert -- an --, therefor.

In column 10, line 12, in Claim 20, delete "The method of claim" and insert -- The image reconstruction apparatus of claim --, therefor.

Signed and Sealed this
Twentieth Day of November, 2012

David J. Kappos
*Director of the United States Patent and Trademark Office*